United States Patent
Sakuragi et al.

(10) Patent No.: US 10,914,845 B2
(45) Date of Patent: Feb. 9, 2021

(54) RADIATION IMAGING APPARATUS

(71) Applicant: CANON KABUSHIKI KAISHA, Tokyo (JP)

(72) Inventors: Shichihei Sakuragi, Kawasaki (JP); Masataka Suzuki, Yokohama (JP); Katsushi Kato, Kawasaki (JP); Hiroto Kondo, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 23 days.

(21) Appl. No.: 16/373,251

(22) Filed: Apr. 2, 2019

(65) Prior Publication Data
US 2019/0310383 A1 Oct. 10, 2019

(30) Foreign Application Priority Data
Apr. 9, 2018 (JP) ................. 2018-074866

(51) Int. Cl.
*G01T 1/175* (2006.01)
*H02J 50/10* (2016.01)
*A61B 6/00* (2006.01)

(52) U.S. Cl.
CPC .......... *G01T 1/175* (2013.01); *A61B 6/4216* (2013.01); *A61B 6/4283* (2013.01); *A61B 6/56* (2013.01); *H02J 50/10* (2016.02)

(58) Field of Classification Search
CPC ........ G01T 1/175; G01T 1/161; H02J 50/10; H02J 50/90; A61B 6/56; A61B 6/4283; A61B 6/4216; A61B 6/4225; A61B 6/4233; A61B 6/4405; A61B 6/44
See application file for complete search history.

(56) References Cited

U.S. PATENT DOCUMENTS

| | | | | |
|---|---|---|---|---|
| 2010/0253153 A1* | 10/2010 | Kondo | ............. | H01F 38/14 307/104 |
| 2014/0226795 A1* | 8/2014 | Kitano | ............. | A61B 6/4283 378/189 |

FOREIGN PATENT DOCUMENTS

| | | |
|---|---|---|
| JP | 2008-170315 A | 7/2008 |
| JP | 2015-166691 A | 9/2015 |
| JP | 2015-197317 A | 11/2015 |
| JP | 2015-197663 A | 11/2015 |

* cited by examiner

*Primary Examiner* — David P Porta
*Assistant Examiner* — Meenakshi S Sahu
(74) *Attorney, Agent, or Firm* — Canon U.S.A., Inc. IP Division (57) ABSTRACT

A radiation imaging apparatus for supplying power in a non-contact manner includes a power reception coil disposed inside a housing together with a radiation detector and a detector contact conductive member, and configured to receive electric energy to be supplied to the radiation detector in a non-contact manner from a power feeding coil disposed outside the housing. The power reception coil is disposed in a second range including a first range in which the detector contact conductive member is formed in the normal direction (y direction) to an incident surface of the radiation detector where the radiation is incident so that an orientation of the center of a generated magnetic flux coincides with an in-plane direction (x direction) of the incident surface and coincides with a direction toward the radiation detector.

13 Claims, 8 Drawing Sheets

RADIATION IMAGING APPARATUS

BACKGROUND OF THE DISCLOSURE

Field of the Disclosure

The disclosure relates to a radiation imaging apparatus used for medical imaging systems, nondestructive inspection apparatuses, and analysis apparatuses.

Description of the Related Art

In the medical field, for example, radiation imaging apparatuses for obtaining a radiation image based on intensity distributions of radiation that penetrated a subject have been widely used. At present, digital radiation imaging apparatuses for acquiring a digital radiation image are used.

The mainstream of methods for supplying power to a digital radiation imaging apparatus includes a method for detaching a detachable battery and connecting the battery to a charger, and a method for supplying power from the connecting portion of the housing to a built-in battery via a cable. In these methods, however, it is necessary to provide waterproofing/dustproofing means at the attaching/detaching portion of the battery and the connecting portion of the cable. This complicates the structure of the imaging apparatus and requires manual operations including a battery attaching/detaching work and a cable connection work.

To eliminate the need of battery attaching/detaching works and cable connection works, there has been studied a method for supplying power (electric energy) to a built-in battery in a non-contact manner. This method supplies power to the battery through magnetic coupling between a power transmission coil and a power reception coil.

Various measures have been taken to improve power feeding efficiency when supplying power in a non-contact manner. Particularly with a digital radiation imaging apparatus, internal conductive members disturb the magnetic flux of the magnetic coupling, decreasing power feeding efficiency.

To handle this concern, for example, a radiation imaging apparatus discussed in Japanese Patent Application Laid-Open No. 2015-197663 has a structure for disposing a partition between an internal shielding member formed of a conductive material and a power reception coil to prevent a magnetic flux from passing through the shielding member. However, there has been an issue that the structure for disposing a partition between the shielding member and the power reception coil increases the size of the housing of the radiation imaging apparatus. Particularly in the current market, there has been increasing demand for decreasing the size and weight of a cassette radiation imaging apparatus in consideration of burden to the engineer using the radiation imaging apparatus. The increase in size of the housing of a radiation imaging apparatus does not meet market demands.

A radiation imaging apparatus discussed in Japanese Patent Application Laid-Open No. 2008-170315 has a structure for making the position of a power reception coil variable. More specifically, the apparatus includes an automatic control mechanism for moving the position of the power reception coil to a position where optimal power feeding efficiency is obtained. However, there has been a concern that the structure for moving the position of the power reception coil requires, for example, a slide mechanism and accordingly increases the size of the housing of the radiation imaging apparatus.

SUMMARY OF THE INVENTION

The disclosure has been developed in view of the above-described concerns, and is directed to offering a mechanism for reducing the size of a housing while preventing a decrease in power feeding efficiency in a radiation imaging apparatus for supplying power in a non-contact manner.

A radiation imaging apparatus according to the disclosure includes a radiation detector configured to detect incident radiation and convert the radiation into an image signal, a conductive member disposed in contact with the radiation detector, and a power reception coil disposed inside a housing together with the radiation detector and the conductive member, and configured to receive electric energy to be supplied to the radiation detector in a non-contact manner from a power feeding coil disposed outside the housing. In a second range including a first range in which the conductive member is formed in the normal direction to an incident surface of the radiation detector where the radiation is incident, the power reception coil is disposed so that an orientation of the center of a generated magnetic flux coincides with an in-plane direction of the incident surface and coincides with a direction toward the radiation detector.

Further features and aspects of the disclosure will become apparent from the following description of numerous example embodiments with reference to the attached drawings.

DESCRIPTION OF THE EMBODIMENTS

Example embodiments and aspects of the disclosure will herein now be described below with reference to the accompanying drawings.

Figure 1:
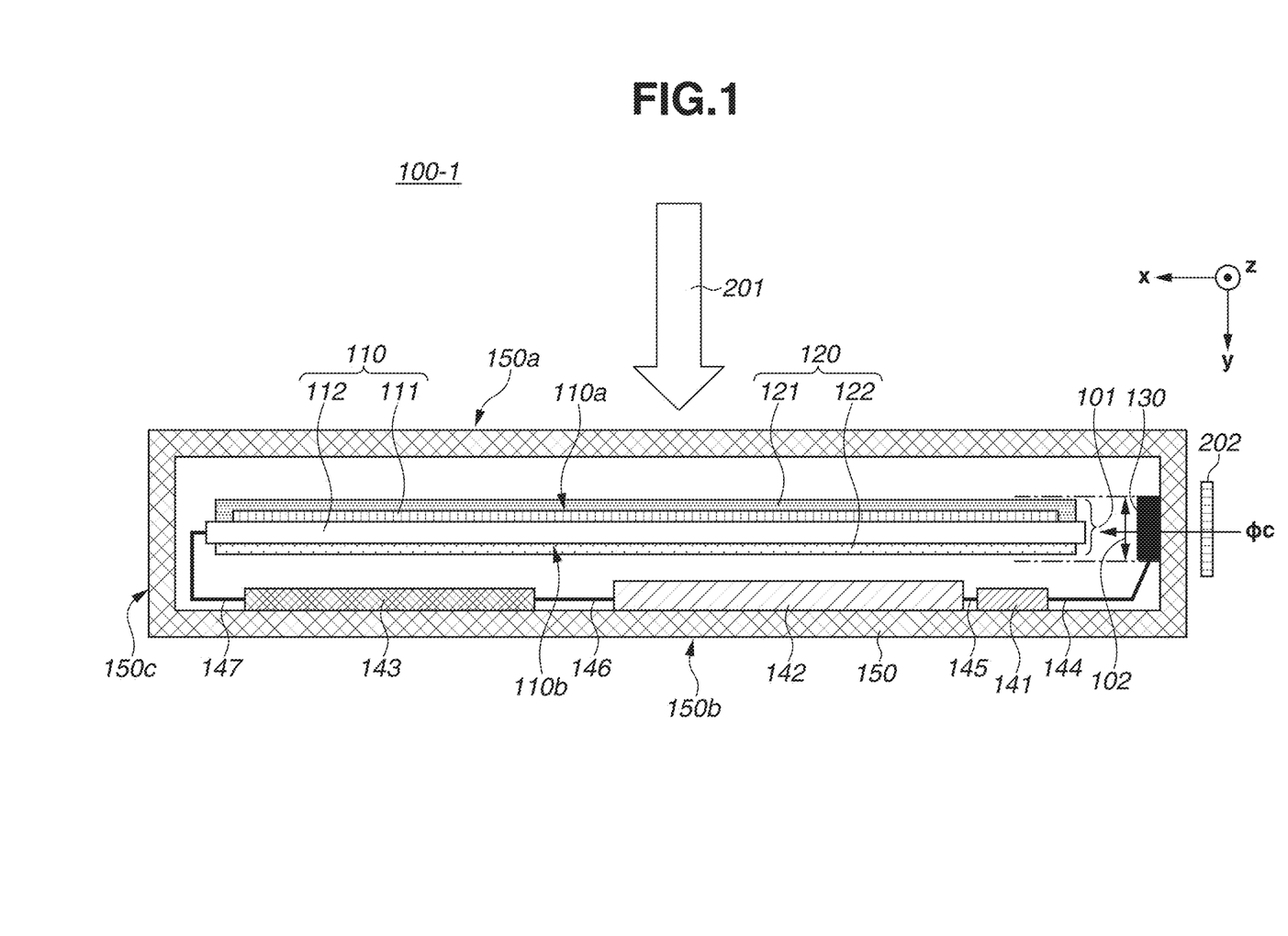
FIG. 1 illustrates an example of a schematic configuration of a radiation imaging apparatus according a first example embodiment of the disclosure.

FIG. 1 illustrates an example of a schematic configuration of a radiation imaging apparatus (hereinafter, simply referred to as an imaging apparatus) 100-1 according to a first example embodiment of the disclosure. FIG. 1 illustrates an xyz coordinate system including the y direction in which a radiation 201 enters the imaging apparatus 100-1, and the x and z directions perpendicular to the y direction. FIG. 1 also illustrates a cross section of the imaging apparatus 100-1 in the xy plane.

The imaging apparatus 100-1 includes a radiation detector (hereinafter simply referred to as a detector) 110, a detector contact conductive member 120, a power reception coil 130, a battery substrate 141, a battery 142, a control substrate 143, wires 144 to 147, and a housing 150.

The detector 110 detects the incident radiation 201 and converts the radiation 201 into an image signal. The detector 110 includes a phosphor 111 and an optical detection unit 112. The surface of the housing 150 of the imaging apparatus 100-1 where the radiation 201 is incident is referred to as a "housing incident surface 150a", and the surface of the housing 150 facing the incident surface 150a is referred to as a "housing rear surface 150b". The phosphor 111, a component disposed on the side of the housing incident surface 150a, converts the radiation 201 into light. The optical detection unit 112, a component disposed on the side of the housing rear surface 150b, detects the light generated by the phosphor 111 and converts the light into an image signal. The surface of the detector 110 where the radiation 201 is incident is referred to as a "detector incident surface 110a", and the surface of the detector 110 facing the detector incident surface 110a is referred to as a "detector rear surface 110b". According to the present example embodiment, the in-plane direction of the detector incident surface 110a and the in-plane direction of the detector rear surface 110b are parallel to the x direction.

The detector contact conductive member 120 is disposed in contact with the detector 110. The detector contact conductive member 120 includes a conductive sheet 121 and a shielding member 122.

The conductive sheet 121 is an incident surface side conductive member disposed in contact with the detector incident surface 110a. More specifically, the conductive sheet 121 is disposed in contact with the detector incident surface 110a (phosphor 111) so as to include the phosphor 111. The conductive sheet 121 covers the phosphor 111 to provide moisture-proof effects and serve the function of an electromagnetic shield to disturbance noise entering the optical detection unit 112. More specifically, the conductive sheet 121 is a conductive member having a function of restraining disturbance to the detector 110. While Al alloy or Cu alloy having high conductivity is suitably used as the conductive sheet 121, other conductive materials are also applicable.

The shielding member 122 is a rear side conductive member disposed in contact with the detector rear surface 110b. More specifically, the shielding member 122 is disposed in contact with the optical detection unit 112 disposed on the detector rear surface 110b. The shielding member 122 shields the radiation 201 which entered without being converted to light by the phosphor 111, so that the radiation 201 does not transmit toward the side of the housing rear surface 150b. For example, in a case where the shielding member 122 is not provided and the radiation 201 transmits toward the side of the housing rear surface 150b, the radiation reflected by the housing rear surface 150b is converted into light by the phosphor 111. This light may become noise in the image signal generated by the optical detection unit 112. More specifically, the shielding member 122 is a conductive member having a function of restraining disturbance to the detector 110. For example, the shielding member 122 is made of alloy containing a heavy metal having high radiation shielding effects, such as Pb, Mo, and W, or stainless steel thickened to such an extent that sufficient radiation shield effects can be acquired.

The power reception coil (power reception unit) 130 disposed inside the housing 150 receives electric energy to be supplied to the detector 110 in a non-contact manner from a power feeding coil 202 disposed outside of the housing 150. The power reception coil 130 is disposed in a second range 102 including a first range 101 in which the detector contact conductive member 120 is formed along the normal direction to the detector incident surface 110a (i.e., y direction). The power reception coil 130 is disposed so that the orientation of a magnetic flux Φc passing through the center in the normal direction (y direction) to the detector incident surface 110a coincides with the in-plane direction (x direction) of the detector incident surface 110a and coincides with the direction toward the detector 110. In other words, the power reception coil 130 is disposed so that the orientation of the center of the generated magnetic flux Φc coincides with the in-plane direction (x direction) of the detector incident surface 110a and coincides with the direction toward the detector 110. The detector 110 is included in the second range 102.

The power reception coil 130 may be disposed inside a side surface 150c connecting the housing incident surface 150a and the housing rear surface 150b, may be disposed at a position including the center of the side surface 150c in the longitudinal direction, and may be disposed at a position including the center of the side surface 150c in the widthwise direction.

The battery substrate 141 is connected with the power reception coil 130 via the wire 144. The battery substrate 141 is supplied with a current output from the power reception coil 130. This current is generated by the induced electromotive force generated by the magnetic flux generated in the power reception coil 130 by the power feeding coil 202 disposed outside of the housing 150.

The battery 142 is connected with the battery substrate 141 via the wire 145. The electric energy of the battery 142 is charged by the current flowing through the battery substrate 141. This current is generated by the induced electromotive force generated by the magnetic flux generated in the power reception coil 130 by the power feeding coil 202.

The control substrate 143 is connected with the battery 142 via the wire 146 and connected with the optical detection unit 112 via the wire 147. The control substrate 143 operates on the electric energy received from the battery 142 via the wire 146. The control substrate 143 supplies electric energy, for example, to the detector 110 (optical detection unit 112) via the wire 146, acquires an image signal from the optical detection unit 112, and processes the image signal as required to generate a radiation image.

As illustrated in FIG. 1, the housing 150 is a box for storing the detector 110, the detector contact conductive member 120, the power reception coil 130, the battery substrate 141, the battery 142, the control substrate 143, and the wires 144 to 147.

The power feeding efficiency by the arrangement of the power reception coil 130 will be described below.

Figure 2:
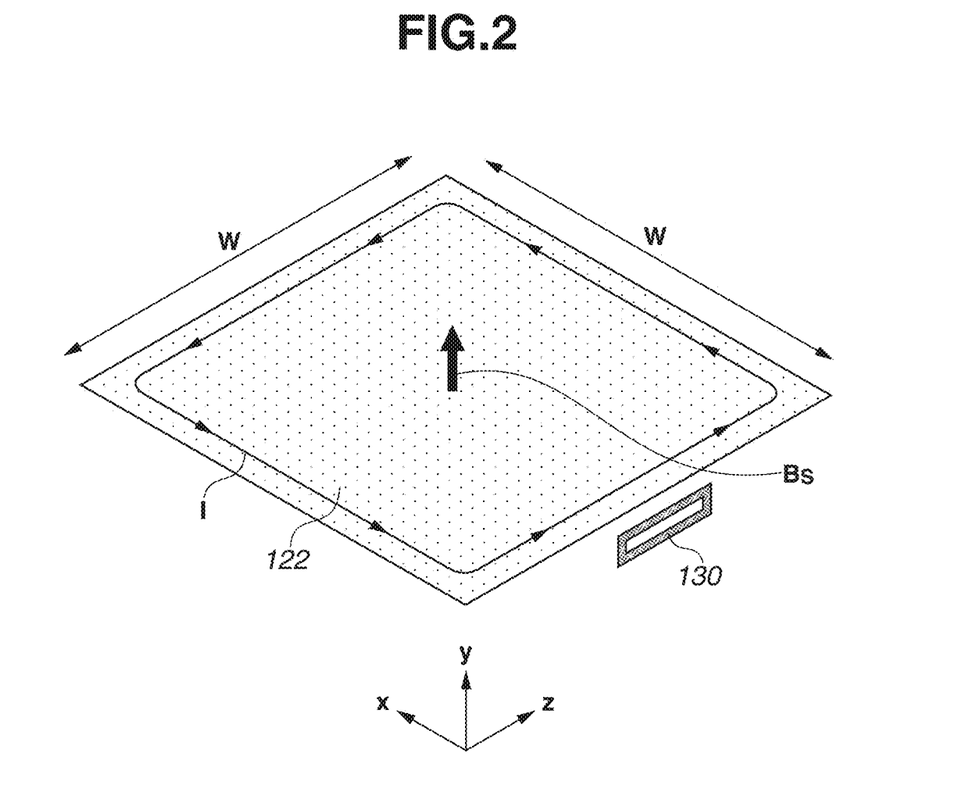
FIG. 2 illustrates the first example embodiment of the disclosure, more particularly, a relation between a power reception coil, a detector contact conductive member, and a magnetic flux illustrated in FIG. 1.
Figure 3:
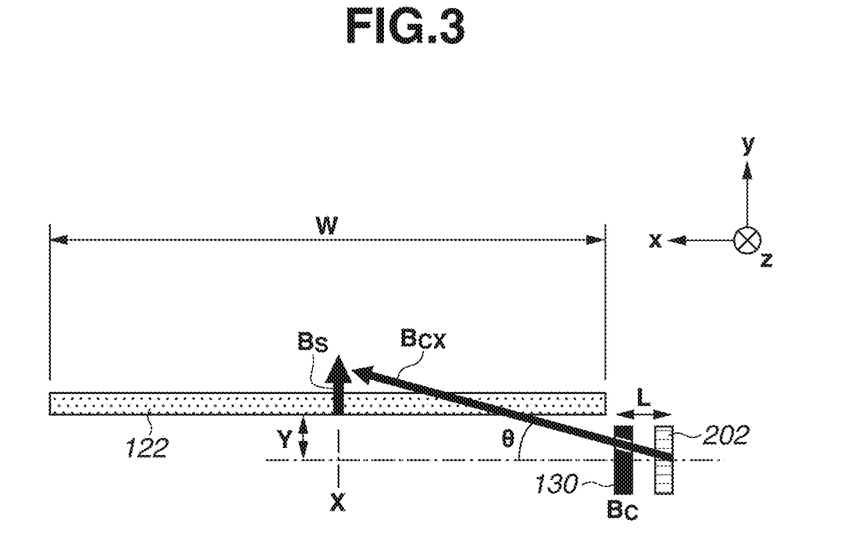
FIG. 3 illustrates the first example embodiment of the disclosure, more particularly, another relation between the power reception coil, the detector contact conductive member, and the magnetic flux illustrated in FIG. 1.

FIGS. 2 and 3 illustrate a relation between the power reception coil 130, the detector contact conductive member 120, and the magnetic flux illustrated in FIG. 1. Referring to FIGS. 2 and 3, configurations equivalent to those illustrated in FIG. 1 are assigned the same reference numerals. FIGS. 2 and 3 illustrate the xyz coordinate system corresponding to the xyz coordinate system illustrated in FIG. 1, and illustrate the shielding member 122 among the conductive members forming the detector contact conductive member 120.

If an eddy current I flowing in the shielding member 122 illustrated in FIG. 2 generates a large magnetic flux Φ, the current flowing in the power reception coil 130 fluctuates, decreasing power feeding efficiency.

The magnitude of the magnetic flux Φ generated in the shielding member 122 is obtained. The eddy current I flowing in the shielding member 122 and the magnetic flux Φ will be described below with reference to FIGS. 2 and 3. The same applies to eddy current and magnetic flux of the conductive sheet 121.

The magnetic flux Φ is in inverse proportion to the square of distance. As illustrated in FIG. 3, when a magnetic flux density Bc is present at the position of the power reception coil 130, a magnetic flux density Bcx at the position of a distance X in the x-direction from the power reception coil 130 can be represented by the following formula (1):

[Numerical Expression 1]

$$Bcx = Bc \times \frac{1}{x^2} \qquad (1)$$

When decomposed into a vector component, a magnetic flux density Bs of the shielding member 122 at the position of a distance X in the x-direction from the power reception coil 130 can be represented by the following formula (2):

[Numerical Expression 2]

$$Bs = Bs \times \sin\theta = Bcx \times \frac{y}{x} \qquad (2)$$

Therefore, when the power feeding coil 202 and the power reception coil 130 are disposed at a distance L in an x-direction from each other, and the shielding member 122 and the power feeding coil 202 and the power reception coil 130 are disposed at a distance Y in a y-direction from each other, the magnetic flux Φ penetrating the shielding member 122 having a length W of one side illustrated in FIG. 2 can be represented by the following formula (3):

[Numerical Expression 3]

$$\Phi = \int_L^{W+L} B_c \cdot \frac{1}{x^2} \cdot \frac{Y}{x} dx = YB_c \int_L^{W+L} \frac{1}{x^3} dx \qquad (3)$$

$$= -\frac{YB_c}{2} \cdot \left( \frac{1}{(W+L)^2} - \frac{1}{L^2} \right)$$

$$= \frac{Y}{2L^2} B_c$$

$$\left( \because \frac{1}{(W+L)^2} \ll \frac{1}{L^2} \right)$$

Referring to formula (3), when the distance L is constant, the magnetic flux Φ generated in the shielding member 122 increases with increasing distance Y, possibly decreasing power feeding efficiency in non-contact power feeding.

According to the present example embodiment, to reduce the distance Y, the power reception coil 130 is disposed in the second range 102 including the first range 101 in which the detector contact conductive member 120 is formed in the normal direction to the detector incident surface 110a (y direction), as illustrated in FIG. 1. This enables preventing a decrease in power feeding efficiency.

As the mainstream, the power reception coil 130 is thinly formed as a sheet-like member in the direction of the magnetic flux Φc (x direction). Therefore, it is not necessary to provide a large space for the power reception coils 130 near the detector 110, thus reducing the size of the housing 150.

With the imaging apparatus 100 for supplying power in a non-contact manner according to the present example embodiment, it is possible to reduce the size (and weight) of the housing 150 while preventing a decrease in power feeding efficiency.

A second example embodiment will be described below centering on differences from the above-described first example embodiment. Redundant descriptions of elements equivalent to those in the first example embodiment will be omitted.

Figure 4:
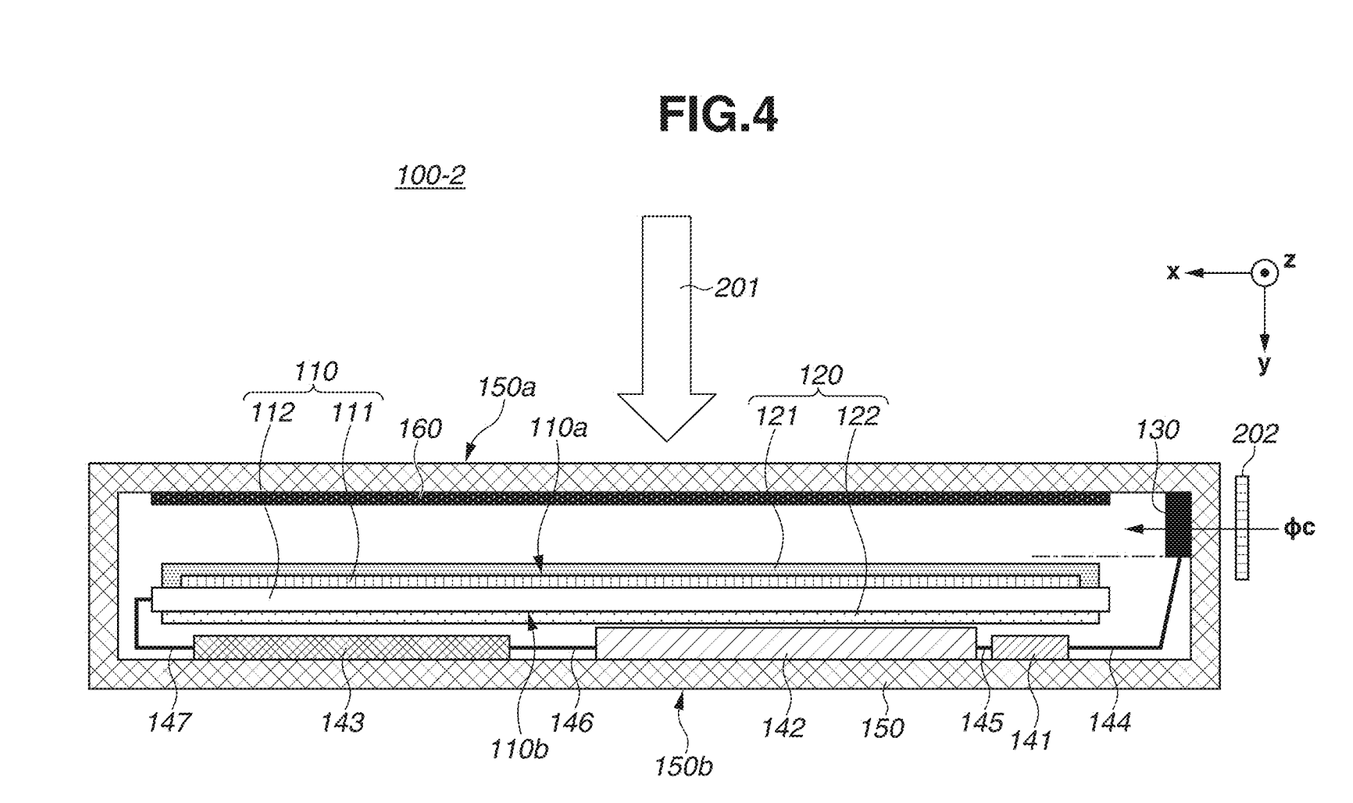
FIG. 4 illustrates an example of a schematic configuration of a radiation imaging apparatus according to a second example embodiment of the disclosure.

FIG. 4 illustrates an example of a schematic configuration of a radiation imaging apparatus 100-2 according to the second example embodiment of the disclosure. Referring to FIG. 4, elements equivalent to those in the first example embodiment illustrated in FIG. 1 (and FIGS. 2 and 3) are assigned the same reference numerals, and detailed descriptions thereof will be omitted.

The imaging apparatus 100-2 according to the second example embodiment includes a shield substrate 160 in addition to the configuration of the imaging apparatus 100-1 according to the first example embodiment.

The detector contact conductive member 120 is equivalent to a first conductive member disposed in contact with the detector 110. The shield substrate 160, a conductive member not in contact with the detector 110 and the detector contact conductive member 120, is equivalent to a second conductive member formed at a position different from the position of the detector contact conductive member 120 in the normal direction (y direction) to the detector incident surface 110a. More specifically, the shield substrate 160 is disposed inside the housing 150, more on the side of the housing incident surface 150a than the detector contact conductive member 120 formed by the conductive sheet 121 and the shielding member 122 in the normal direction to the detector incident surface 110a (y direction). The shield substrate 160 is disposed as a disturbance noise measure in the detector 110. In other words, the shield substrate 160 is a conductive member having a function of preventing disturbance to the detector 110.

The power reception coil 130 is disposed between a first position where the detector contact conductive member 120 is disposed and a second position where the shield substrate 160 is disposed in the normal direction to the detector incident surface 110a (y direction). The power reception coil 130 is disposed so that the orientation of a magnetic flux Φc passing through the center in the normal direction (y direction) to the detector incident surface 110a coincides with the in-plane direction (x direction) of the detector incident surface 110a and coincides with the direction toward the detector 110. In other words, the power reception coil 130 is disposed so that the orientation of the center of the generated magnetic flux Φc coincides with the in-plane direction (x direction) of the detector incident surface 110a and coincides with the direction toward the facing side surface 150c.

The magnetic flux generated in the power reception coil 130 will be affected by the magnetic flux generated by both conductive members, the shield substrate 160 and the detector contact conductive member 120. The following describes a case where the conductivity of the shield substrate 160 is higher than the conductivity of the detector contact conductive member 120. In this case, the magnetic flux generated in the shield substrate 160 is larger than the magnetic flux generated in the detector contact conductive member 120, and accordingly the magnetic flux generated in the power reception coil 130 will be more largely affected by the magnetic flux in the shield substrate 160 than by the magnetic flux in the detector contact conductive member 120.

As described above, the magnetic flux in the power reception coil 130 is affected by a plurality of conductive members (the detector contact conductive member 120 and the shield substrate 160). Therefore, when there is a distance between the two conductive members, the power reception coil 130 is disposed at a position closer to the position of the shield substrate 160 having high conductivity than to the position of the detector contact conductive member 120 having low conductivity in the normal direction (y direction) to the detector incident surface 110a. For more detail, to minimize the y-direction distance to the shield substrate 160 having high conductivity (distance equivalent to the distance Y illustrated in FIG. 3), the y-direction position of the power reception coil 130 is matched with the y-direction position of the shield substrate 160.

While the present example embodiment has been described above centering on a case where the conductivity of the shield substrate 160 is higher than the conductivity of the detector contact conductive member 120, the disclosure is not limited thereto. A case where the conductivity of the detector contact conductive member 120 is higher than the conductivity of the shield substrate 160 is also applicable to the disclosure. When this form is employed, in contrast to the example illustrated in FIG. 4, to minimize the y-direction distance to the detector contact conductive member 120 having high conductivity, the y-direction position of the power reception coil 130 may be matched with the y-direction position of the detector contact conductive member 120.

According to the second example embodiment, it is possible to reduce the size (and weight) of the housing 150 while preventing a decrease in power feeding efficiency.

A third example embodiment will be described below centering on differences from the above-described first and second example embodiments. Redundant descriptions of elements equivalent to those in the first and the second example embodiments will be omitted.

Figure 5:
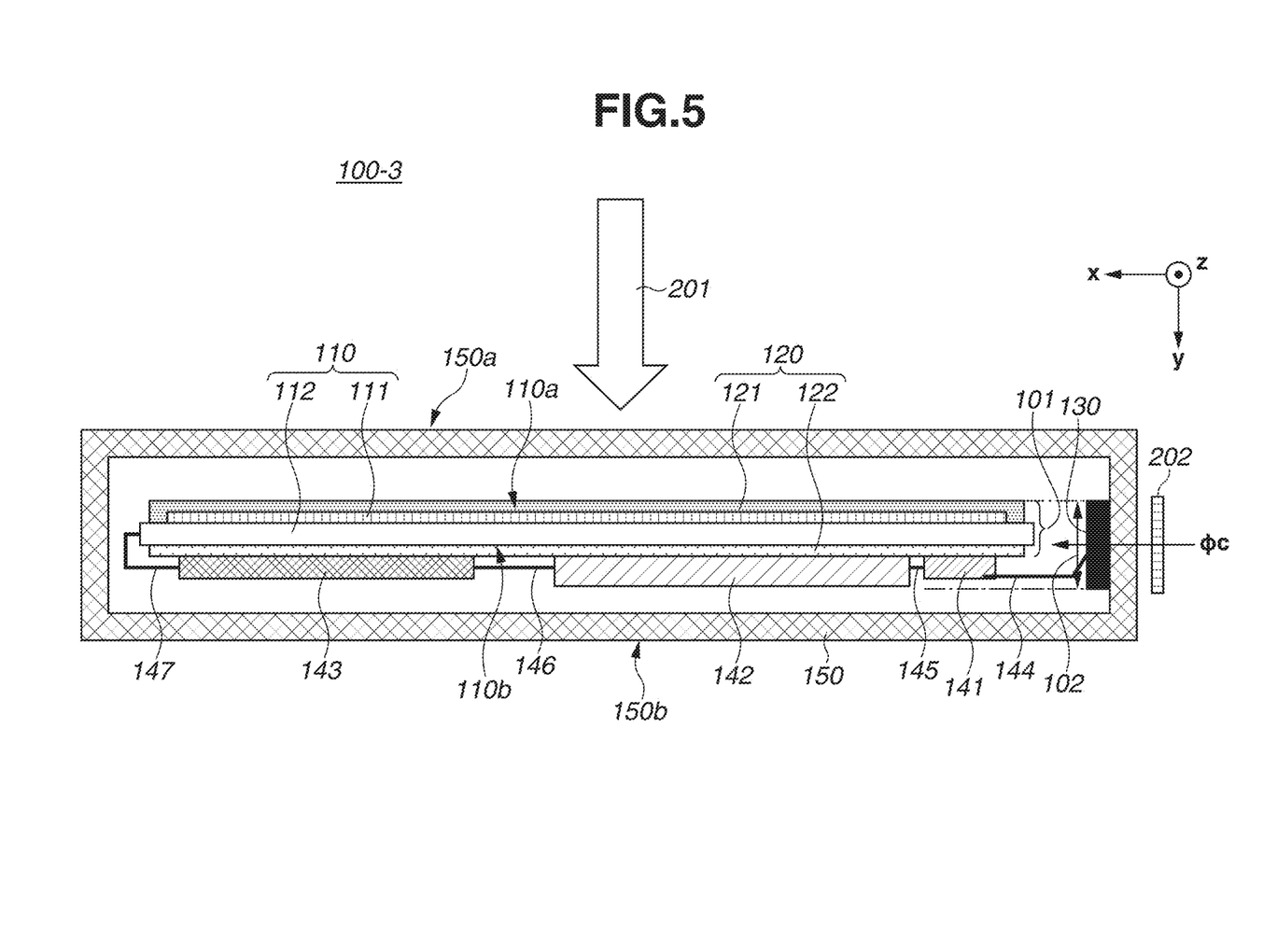
FIG. 5 illustrates an example of a schematic configuration of a radiation imaging apparatus according to a third example embodiment of the disclosure.

FIG. 5 illustrates an example of a schematic configuration of a radiation imaging apparatus 100-3 according to the third example embodiment of the disclosure. Referring to FIG. 5, elements equivalent to those in the first example embodiment illustrated in FIG. 1 (and FIGS. 2 and 3) are assigned the same reference numerals, and detailed descriptions thereof will be omitted.

The imaging apparatus 100-3 according to the third example embodiment includes the configuration of the imaging apparatus 100-1 according to the first example embodiment in which the battery substrate 141, the battery 142, the control substrate 143, and the wires 144 to 147 are moved toward the side of the housing incident surface 150a and deviated toward the side of the rear surface of the shielding member 122.

Currents flowing in these substrates (the battery substrate 141 and the control substrate 143) and the battery 142 generate magnetic fluxes, affecting the magnetic flux of the power reception coil 130. The third example embodiment assumes further preventing a decrease in power feeding efficiency taking into consideration the influences by the magnetic fluxes in these substrates (the battery substrate 141 and the control substrate 143) and the battery 142. More specifically, according to the third example embodiment illustrated in FIG. 5, the power reception coil 130 is disposed in the first range 101 in which the detector contact conductive member 120 is formed, in the normal direction (y direction) to the detector incident surface 110a. The power reception coil 130 is also disposed in the second range 102 including the range in which the battery substrate 141, the battery 142, the control substrate 143, and the wires 144 to 147 are formed.

According to the third example embodiment, it is possible to further prevent the decrease in power feeding efficiency while achieving the effects of the above-described first example embodiment.

A fourth example embodiment of the disclosure will be described below. The fourth example embodiment will be described below centering on differences from the above-described first to third example embodiments. Redundant descriptions of elements equivalent to those in the first to the third example embodiments will be omitted.

Figure 6:
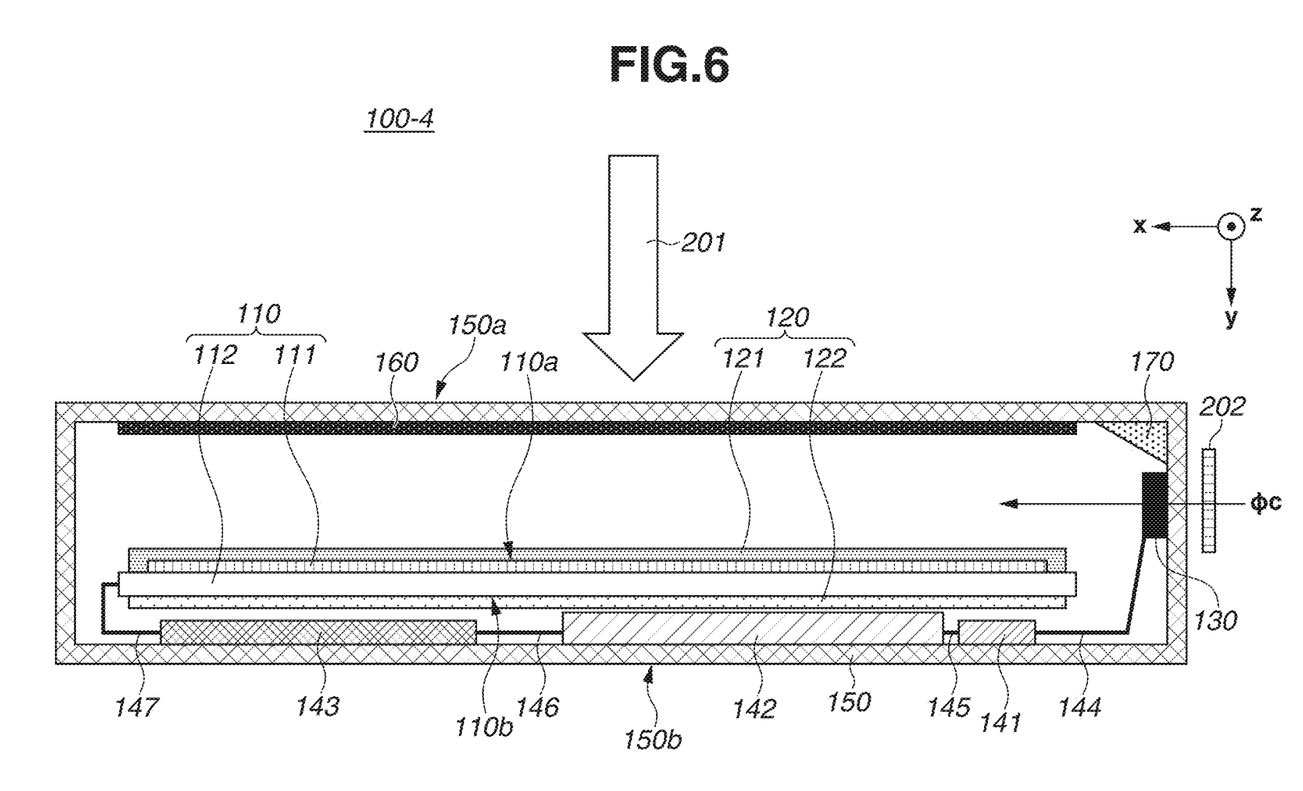
FIG. 6 illustrates an example of a schematic configuration of a radiation imaging apparatus according to a fourth example embodiment of the disclosure.

FIG. 6 illustrates an example of a schematic configuration of a radiation imaging apparatus 100-4 according to the fourth example embodiment of the disclosure. Referring to FIG. 6, elements equivalent to those in the second example embodiment illustrated in FIG. 4 are assigned the same reference numerals, and detailed descriptions thereof will be omitted.

The imaging apparatus 100-4 according to the fourth example embodiment includes a structure 170 in addition to the configuration of the imaging apparatus 100-2 according to the second example embodiment.

The structure 170 is disposed to improve the rigidity of the housing 150. The structure 170 may be, for example, a thick-wall structure, rib, or a wire connected to the substrates. The structure 170 is disposed inside the housing 150, in connection with the housing incident surface 150a. Accordingly, like the imaging apparatus 100-2 illustrated in FIG. 4, the y-direction position of the power reception coil 130 may be unable to be matched with the y-direction position of the shield substrate 160.

In the imaging apparatus 100-4 according to the fourth example embodiment, therefore, the power reception coil 130 is disposed so that the position of the center of the power reception coil 130 in the normal direction (y direction) to the detector incident surface 110a approximately coincides with the position of the center between the first position where the detector contact conductive member 120 is disposed and the second position where the shield substrate 160 is disposed. In this case, for example, the position of the center between the position where the conductive sheet 121 is disposed and the position where the shielding member 122 is disposed can be taken as the first position where the detector contact conductive member 120 is disposed.

Figure 7:
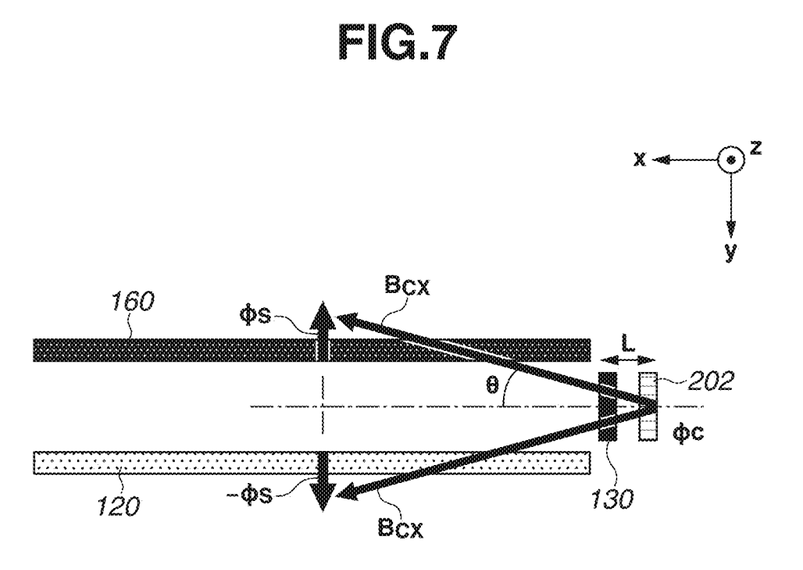
FIG. 7 illustrates the fourth example embodiment of the disclosure, more particularly, a relation between a power reception coil, a detector contact conductive member, a shield substrate, and a magnetic flux illustrated in FIG. 6.

FIG. 7 illustrates the fourth example embodiment of the disclosure, more particularly, a relation between the power reception coil 130, the detector contact conductive member 120, the shield substrate 160, and the magnetic flux illustrated in FIG. 6.

Under the influence of the magnetic flux $\Phi c$ generated in the power reception coil 130, currents flow in the shield substrate 160 and the detector contact conductive member 120 by the induced electromotive force, and, for example, a magnetic flux $\Phi s$ and a magnetic flux $-\Phi s$ may be generated. In this case, the magnetic flux generated in the shield substrate 160 and the magnetic flux generated in the detector contact conductive member 120 have the same magnitude and opposite directions. In this case, the magnetic fluxes generated in opposite directions affect and cancel each other, providing effects of preventing the influence on the magnetic flux generated in the power reception coil 130 and preventing a decrease in power feeding efficiency.

With the imaging apparatus 100 for supplying power in a non-contact manner according to the fourth example embodiment, like the above-described second example embodiment, it is possible to reduce the size (and weight) of the housing 150 while preventing a decrease in power feeding efficiency.

A fifth example embodiment will be described below centering on differences from the above-described first to fourth example embodiments. Redundant descriptions of elements equivalent to those in the first to the fourth example embodiments will be omitted.

Figure 8:
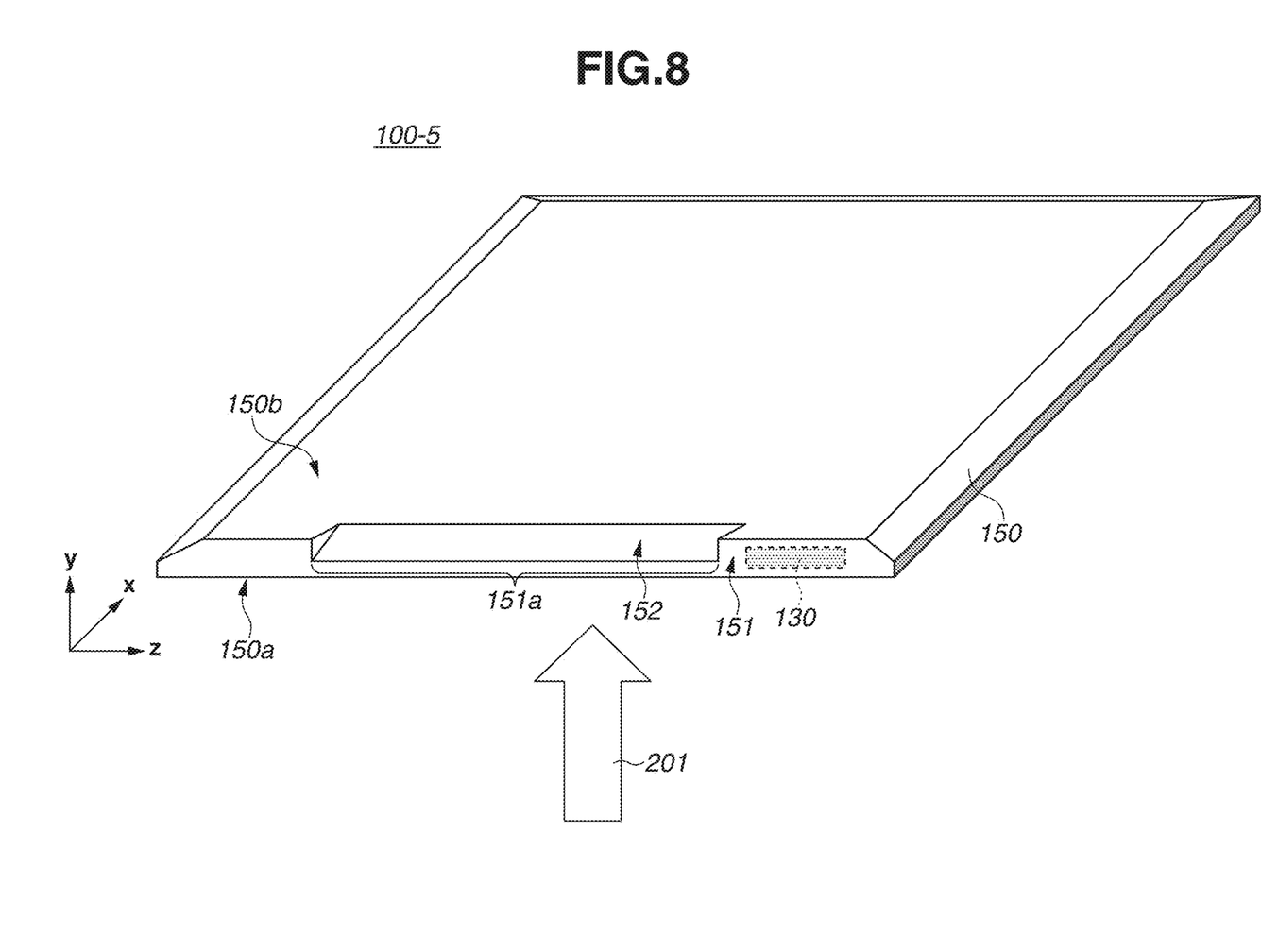
FIG. 8 illustrates an example of an external configuration of a radiation imaging apparatus according to a fifth example embodiment of the disclosure.

FIG. 8 illustrates an example of an external configuration of a radiation imaging apparatus 100-5 according to the fifth example embodiment of the disclosure. Referring to FIG. 8, elements equivalent to those in the first to the fourth example embodiments illustrated in FIGS. 1 to 7 are assigned the same reference numerals, and detailed descriptions thereof will be omitted. The radiation 201 is incident from the underside to the upper side of paper.

In the housing 150, the power reception coil 130 is disposed in a surface 151 parallel to the normal direction (y direction) to the detector incident surface 110a according to the first to the fourth example embodiments.

In a cassette imaging apparatus 100, as the mainstream, the surface connecting the incident surface 150a and the housing rear surface 150b is inclined with respect to the housing incident surface 150a or rounded in consideration of the operator's workability. When a cassette imaging apparatus 100 is placed on a flat surface, the operator can smoothly handle the housing 150 by holding this inclined or rounded portion.

Accordingly, in consideration of the operator's workability, a slope 152 inclined with respect to the above-described normal direction (y direction) is connected to an area 151a of the surface 151 where the power reception coil 130 is not disposed. In consideration of the center of gravity of the cassette imaging apparatus 100 existing in the approximate central portion of the housing 150, the slope 152 is provided in the area 151a near the z-direction center of the surface 151. This structure makes it easier for the operator to hold the central portion of the housing 150 and accordingly to smoothly handle the imaging apparatus 100. In the above-described configuration, the slope 152 is connected to the area 151a. Alternatively, a form of providing a rounded portion instead of the slope 152 is also applicable to the disclosure.

According to the fifth example embodiment, it is possible to improve the operator's workability while achieving the effects of the first to the fourth example embodiments.

While the disclosure has been described with reference to example embodiments, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2018-074866, filed Apr. 9, 2018, which is hereby incorporated by reference herein in its entirety.

What is claimed is:

1. A radiation imaging apparatus comprising:
a housing;
a radiation detector disposed inside the housing and configured to detect incident radiation and convert the radiation into an image signal;
a conductive member disposed inside the housing and in contact with the radiation detector; and
a power reception coil disposed inside the housing and configured to receive electric energy to be supplied to the radiation detector in a non-contact manner from a power feeding coil disposed outside the housing,
wherein, the power reception coil is disposed in a second range including a first range in which the conductive member is formed in the normal direction to an incident surface of the radiation detector where the radiation is incident.

2. The radiation imaging apparatus according to claim 1, wherein the conductive member comprises:
an incident surface side conductive member disposed in contact with the incident surface of the radiation detector; and
a rear side conductive member disposed in contact with a rear surface of the radiation detector facing the incident surface.

3. The radiation imaging apparatus according to claim 2, wherein the radiation detector comprises:
a phosphor disposed on the side of the incident surface, and configured to convert the radiation into light; and
an optical detection unit disposed on the side of the rear surface, and configured to detect the light and convert the light into an image signal,
wherein the incident surface side conductive member is disposed in contact with the phosphor so as to include the phosphor, and
wherein the rear side conductive member is disposed in contact with the optical detection unit.

4. The radiation imaging apparatus according to claim 1, wherein the radiation detector is included in the second range.

5. The radiation imaging apparatus according to claim 1, wherein the second range includes a battery substrate connected with the power reception coil via a wire.

6. The radiation imaging apparatus according to claim 1, wherein the housing comprises an incident surface where radiation is incident, a rear surface facing the incident surface, and a side surface connecting the incident and the rear surfaces, and
wherein the power reception coil is disposed inside the side surface, and is disposed at a position including the center of the side surface in the longitudinal direction.

7. The radiation imaging apparatus according to claim 6, wherein the power reception coil is disposed at a position including the center of the side surface in the widthwise direction.

8. A radiation imaging apparatus comprising:
a housing;
a radiation detector disposed inside the housing and configured to detect incident radiation and convert the radiation into an image signal;
a first conductive member disposed inside the housing and in contact with the radiation detector;
a second conductive member not in contact with the radiation detector and the first conductive member, disposed inside the housing at a position different from the position of the first conductive member in the normal direction to the incident surface of the radiation detector where the radiation is incident; and a power reception coil disposed inside the housing, wherein the power reception coil receives electric energy to be supplied to the radiation detector in a non-contact manner from a power feeding coil disposed outside the housing, and wherein the power reception coil is disposed between a first position where the first conductive member is disposed and a second position where the second conductive member is disposed in the normal direction so that an orientation of the center of a generated magnetic flux coincides with an in-plane direction of the incident surface.

9. The radiation imaging apparatus according to claim 8, wherein, in a case where the first and the second conductive members are different in conductivity, the power reception coil is disposed at a position closer to a position of the conductive member having higher conductivity than to a position of the conductive member having lower conductivity in the normal direction among the first and the second conductive members.

10. The radiation imaging apparatus according to claim 8, wherein, in the normal direction, a position of the center of the power reception coil approximately coincides with a position of the center between the first and the second positions.

11. The radiation imaging apparatus according to claim 8, wherein the housing comprises an incident surface where radiation is incident, a rear surface facing the incident surface, and a side surface connecting the incident and the rear surfaces, and wherein the power reception coil is disposed inside a first side surface, at a position including the center of the first side surface in the longitudinal direction, in a manner that an orientation of the center of a magnetic flux coincides with a direction toward a second side surface facing the first side surface.

12. The radiation imaging apparatus according to claim 1, wherein, in the housing, the power reception coil is disposed in a surface parallel to the normal direction, and wherein a slope inclined with respect to the normal direction is connected to an area of the parallel surface where the power reception coil is not disposed.

13. The radiation imaging apparatus according to claim 1, wherein an orientation of the center of a generated magnetic flux coincides with an in-plane direction of the incident surface and coincides with a direction toward the radiation detector.

* * * * *